(12) United States Patent
Kelp et al.

(10) Patent No.: US 12,076,232 B2
(45) Date of Patent: Sep. 3, 2024

(54) INJECTOR HAVING A FIRST PISTON AND A SECOND PISTON

(71) Applicant: Carl Zeiss Meditec AG, Jena (DE)

(72) Inventors: Martin Kelp, Berlin (DE); Alfred Rinman, Hamburg (DE); Hadi Moein, Berlin (DE); Niklas Damm, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/540,439

(22) Filed: Dec. 14, 2023

(65) Prior Publication Data
US 2024/0108457 A1 Apr. 4, 2024

Related U.S. Application Data

(63) Continuation of application No. PCT/EP2022/066976, filed on Jun. 22, 2022.

(30) Foreign Application Priority Data

Jun. 28, 2021 (DE) ...................... 10 2021 116 615.2

(51) Int. Cl.
*A61F 2/16* (2006.01)

(52) U.S. Cl.
CPC ............ *A61F 2/167* (2013.01); *A61F 2/1672* (2013.01)

(58) Field of Classification Search
CPC ...... A61F 2/167; A61F 2/1672; A61F 2/1661; A61F 2/1691
See application file for complete search history.

(56) References Cited

U.S. PATENT DOCUMENTS

| 5,190,552 A | 3/1993 | Kelman |
| 9,700,407 B2 | 7/2017 | Safabash |
| (Continued) | | |

FOREIGN PATENT DOCUMENTS

| CN | 112826636 A | 5/2021 |
| EP | 2 340 786 A1 | 7/2011 |
| WO | 00/40175 A1 | 7/2000 |

OTHER PUBLICATIONS

English translation and Written Opinion of the International Searching Authority dated Oct. 17, 2022 for international application PCT/EP2022/066976 on which this application is based.

(Continued)

*Primary Examiner* — Darwin P Erezo
*Assistant Examiner* — Brigid K Byrd
(74) *Attorney, Agent, or Firm* — Walter Ottesen, P.A.

(57) ABSTRACT

An injector for inserting an intraocular lens into a capsular bag of an eye includes an injector body having an injector tip defining an opening. The injector body has a proximal end facing away from the opening and has a distal end. A first piston is directed toward the opening and is configured to contact and displace the intraocular lens. A second piston is operable from outside of the injector and the first piston and the second piston are each configured to be longitudinally displaceable along the injector axis. A handle is operated from outside of the injector and is configured to be coupled to the first piston so that when the pistons are in the decoupling state, the first piston is displaced toward the opening and relative to the second piston by moving the handle.

10 Claims, 5 Drawing Sheets

(56) References Cited

U.S. PATENT DOCUMENTS

| | | | |
|---|---|---|---|
| 2008/0114373 A1* | 5/2008 | Rathert | A61F 2/1691 |
| | | | 606/107 |
| 2010/0125278 A1* | 5/2010 | Wagner | A61F 2/1662 |
| | | | 606/107 |
| 2011/0270264 A1 | 11/2011 | Shoji et al. | |
| 2014/0257317 A1* | 9/2014 | Safabash | A61F 2/1662 |
| | | | 606/107 |
| 2016/0074155 A1 | 3/2016 | Raquin et al. | |
| 2017/0367817 A1* | 12/2017 | Belisle | A61F 2/1672 |
| 2020/0197158 A1* | 6/2020 | Liu | A61F 2/1678 |

OTHER PUBLICATIONS

International Search Report of the European Patent Office dated Oct. 17, 2022 for international application PCT/EP2022/066976 on which this application is based.

English translation and Office action of the Korean Patent Office dated Jan. 26, 2024 for corresponding Korean application No. 10-2024-7000473.

Partial English translation and Office action of the Chinese Patent Office dated Jun. 6, 2024 for corresponding Chinese application No. 2022800459513.

\* cited by examiner

INJECTOR HAVING A FIRST PISTON AND A SECOND PISTON

CROSS REFERENCE TO RELATED APPLICATIONS

This application is a continuation application of international patent application PCT/EP2022/066976, filed Jun. 22, 2022, designating the United States and claiming priority from German application 10 2021 116 615.2, filed Jun. 28, 2021, and the entire content of both applications is incorporated herein by reference.

TECHNICAL FIELD

The disclosure relates to an injector for inserting an intraocular lens into the capsular bag of an eye.

BACKGROUND

In cataract treatment of an eye, only a small incision is usually made in the cornea of the eye, the incision being large enough to allow a tip of an injector to be inserted into the eye through the incision. Once the incision has been made in the cornea, the lens of the eye is comminuted, for example, by phacoemulsification, and then aspirated from the capsular bag of the eye. An intraocular lens is then inserted into the eye. In the process, the intraocular lens is folded such that it fits through the tip of the injector. The tip is inserted into the capsular bag through the incision, and the folded intraocular lens is pushed by a piston of the injector through the tip into the capsular bag in which the intraocular lens unfolds and thus replaces the original lens. The injector is traditionally inserted by hand into the capsular bag and the piston is often manually driven to move it. It would therefore be desirable for the injector to be as easy to operate as possible.

U.S. Pat. No. 9,700,407 B2 discloses an intraocular lens injector. US 2011/0270264 discloses a device for inserting an intraocular lens.

SUMMARY

An object of the disclosure is therefore to provide an injector for inserting an intraocular lens into the capsular bag of an eye, wherein the injector is easy to operate.

An injector according to the disclosure for inserting an intraocular lens into the capsular bag of an eye includes an injector body having an injector tip with an opening and a proximal end facing away from the opening; a first piston which is directed toward the opening and specified to contact and displace the intraocular lens; and a second piston, which is disposed in the region of the proximal end and specified to be able to be operated from outside the injector; wherein the first piston and the second piston are disposed in each case so as to be longitudinally displaceable along an injector axis of the injector in the injector body, either being in a decoupling state in which the pistons can be displaced longitudinally relative to each other, or being in a coupling state in which the pistons are rigidly coupled together in the direction of the injector axis and the total longitudinal extent of the pistons is larger than in the decoupling state. Furthermore, the injector according to the disclosure has a handle which is disposed in a distal region of the injector body and specified to be able to be operated from outside the injector and coupled to the first piston so that when the pistons are in the decoupling state, the first piston is displaceable toward the opening and relative to the second piston by moving the handle such that the pistons can be brought into the coupling state and, by way of contact between the first piston and the intraocular lens, the latter is able to be shifted in the injector tip toward the opening.

As soon as the first piston and the second piston are in the coupling state, the second piston is to be operated by displacing the second piston longitudinally toward the opening. Due to the rigid coupling of the two pistons in the coupling state, the first piston is conjointly displaced accordingly, whereby the intraocular lens is further shifted in the injector tip toward the opening. Once both pistons have reached their terminal position, the intraocular lens has escaped from the opening and can thus be inserted into the capsular bag of an eye.

In that the shifting action of the intraocular lens is divided by the two pistons, it is advantageously possible to embody the second piston shorter in terms of its longitudinal extent. Accordingly, the stroke of the second piston is shorter than the stroke of a conventional injector, in which, for example, only a single piston is provided. Thus, an injector according to the disclosure can be made shorter in its longitudinal extent, whereby the injector is easier to operate than the conventional injector.

Both the handle and the second piston can preferably be operated manually from outside the injector. Because the handle is located in the distal region of the injector body and the second piston is located in the region of the proximal end of the injector body, the handle and the second piston are to be operated from opposite sides. This makes it less likely to accidentally confuse the handle and the second piston during operation, as if the handle and the second piston were to be operated from approximately the same side of the injector. This makes the injector safe and error-free to operate.

The distal region of the injector body here can be formed by a first portion of the injector body, the first portion extending from the opening in the direction of the injector axis by up to 50% of the total longitudinal extent of the injector body. The proximal region of the injector body may be formed by a second portion of the injector body, the second portion extending from the proximal end in the direction of the injector axis by up to 50% of the total longitudinal extent of the injector body.

The injector body has an injector body clearance, wherein the handle extends through the injector body clearance into the interior of the injector body and is directly coupled to the first piston. It can be particularly preferred that the handle is releasably coupled with the first piston. This allows the handle to be removed from the remaining injector before the tip of the injector is inserted into the capsular bag of the eye. Thus, the injector advantageously has no interfering components on the outside of the injector body when the injector tip is inserted into the capsular bag. The handle is envisaged to be removed when the first piston and the second piston have been brought into the coupling state via the handle. It is particularly preferred that the first piston has a piston groove in which the handle engages.

Alternatively, the injector has a slide which is disposed so as to be longitudinally displaceable on the injector body and directly coupled to the first piston, wherein when the handle is moved away from the proximal end, the handle is specified to entrain the slide so that the handle is indirectly coupled to the first piston by way of the slide. It is particularly preferred herein that the slide has a lens holder, which is specified to hold the intraocular lens, wherein when the handle is displaced away from the proximal end and before the handle entrains the slide, the handle is specified to displace the intraocular lens out of the lens holder and fold the intraocular lens. As a result the handle is specified to displace the first piston toward the opening, as well as specified to fold the intraocular lens.

The slide is releasably coupled to the first piston. This allows the slide to be removed from the remaining injector, especially together with the handle, before the tip of the injector is inserted into the capsular bag of the eye. As a result, the injector has no interfering components on the outside of the injector body when the injector tip is inserted into the capsular bag. The slide, and optionally the handle, is/are intended to be removed when the first piston and second piston have been brought into the coupling state via the handle. It can be preferred that the first piston has a piston groove in which the slide engages.

The handle has a cap that delimits an interior space in which the injector body is disposed. Via the cap, the handle is particularly easy to grip by one hand, which makes it particularly easy to move the first piston in the direction of the opening. It can be particularly preferred that the cap protrudes from the injector body in the direction of the injector axis beyond the opening. The cap can particularly preferably have a casing which delimits the interior space in the radial direction with respect to the injector axis, and an end wall which in the direction of the injector axis is disposed next to the injector body and delimits the interior space in the direction of the injector axis. As a result, the injector body is advantageously protected in the distal region.

The second piston on the end side thereof facing the opening preferably can have a piston opening by way of which the first piston extends into the interior of the second piston and on which the first piston in the decoupling state is mounted so as to be longitudinally displaceable relative to the second piston. Alternatively, it is also conceivable that the first piston on the end side thereof facing away from the opening has a piston opening by way of which the second piston extends into the interior of the first piston and on which the second piston in the decoupling state is mounted so as to be longitudinally displaceable relative to the first piston. It is preferable that the pistons are configured to be telescopic. Furthermore, it is preferred that the pistons are disposed coaxially with respect to the injector axis.

The second piston is preferably specified to be displaced longitudinally in the direction of the opening by a pushing movement or a screw movement. Particularly preferably, the second piston is specified so that the pushing movement or the screw movement is to be carried out manually, that is, the injector has no motor, for example.

The injector includes the intraocular lens. The intraocular lens can be disposed in the injector body. In the event that the lens holder is provided, the intraocular lens can alternatively be disposed in the lens holder.

The first piston has a piston protrusion and the second piston has a piston clearance, wherein the piston protrusion is specified to be disposed outside the piston clearance when the first piston and the second piston are in the decoupling state, and is specified to engage in the piston clearance, so as to bring the first piston and the second piston into the coupling state, when the first piston is moved toward the opening. This provides a particularly simple construction that allows the first piston and the second piston to be brought into the coupling state.

BRIEF DESCRIPTION OF DRAWINGS

The invention will now be described with reference to the drawings wherein.

DETAILED DESCRIPTION

Figure 1:
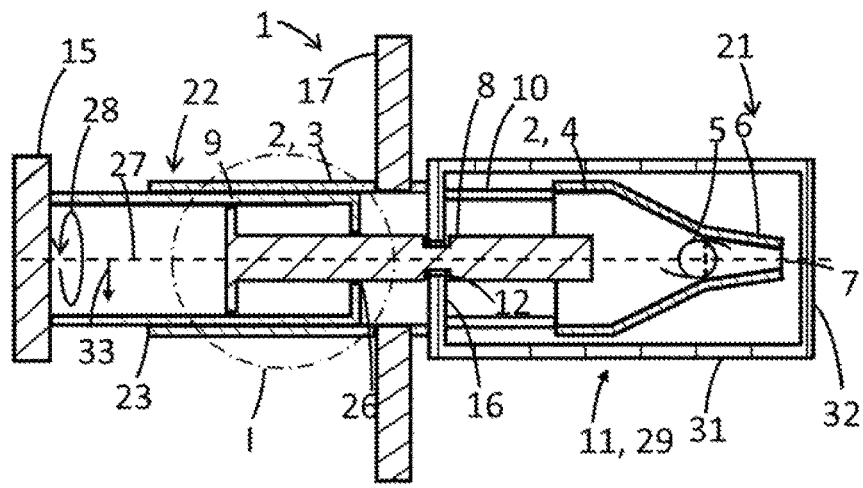
FIG. 1 shows a longitudinal sectional illustration in a view from above of a first embodiment of an injector according to the disclosure at a first point in time.

As can be seen from FIGS. 1 to 12, an injector 1 for inserting an intraocular lens 5 into the capsular bag of an eye has an injector body 2 which has an injector tip 6 with an opening 7 and a proximal end 23 facing away from the opening 7; a first piston 8, which is directed toward the opening 7 and is specified to contact and shift the intraocular lens 5, and a second piston 9 which is disposed in the region of the proximal end 23 and specified to be able to be operated from outside the injector 1. The first piston 8 and the second piston 9 are disposed in each case so as to be longitudinally displaceable along an injector axis 27 of the injector 1 in the injector body 2, either being in a decoupling state in which the pistons 8, 9 can be displaced longitudinally relative to each other, or being in a coupling state in which the pistons 8, 9 are rigidly coupled together in the direction of the injector axis 27 and the total longitudinal extent of the pistons 8, 9 is larger than in the decoupling state. Moreover, the injector 1 has a handle 29 which is disposed in a distal region 21 of the injector body 2 and specified to be able to be operated from outside the injector 1 and coupled to the first piston 8 so that when the pistons 8, 9 are in the decoupling state, the first piston 8 is displaceable toward the opening 7 and relative to the second piston 9 by moving the handle 29 such that the pistons 8, 9 can be brought into the coupling state and, by way of contact between the first piston 8 and the intraocular lens 5, the latter is able to be shifted in the injector tip 6 toward the opening 7.

The distal region 21 of the injector body 2 herein can be formed by a first portion of the injector body 2, wherein the first portion extends from the opening 7 in the direction of the injector axis 27 by up to 50% of the total longitudinal extent of the injector body 2. The proximal region 22 of the injector body 2 herein can be formed by a second portion of the injector body 2, wherein the second portion extends from the proximal end 23 in the direction of the injector axis 27 by up to 50% of the total longitudinal extent of the injector body 2.

FIGS. 1 to 6 and 8 to 10 moreover show that the injector 1 can have an injector handle 17 which is mounted on the injector body 2, protrudes outwardly from the injector body 2 and is disposed in the direction of the injector axis 27 between the proximal end 23 and the handle 29.

FIGS. 1, 2, 4 and 6 to 9 show that the handle 29 can have a cap 11 which delimits an interior space in which the injector body 2 is disposed. The cap 11 can protrude from the injector body 2 in the direction of the injector axis 27 beyond the opening 7. The cap 11 can have a casing 31 which delimits the interior space in the radial direction 33 with respect to the injector axis 27 and in particular delimits the interior space completely in the circumferential direction 28, that is, the casing 31 is embodied without any interruptions in the circumferential direction 28. The circumferential direction 28 and the radial direction 33 are plotted by way of example in FIG. 1. In addition, the cap 11 can have an end wall 32 which in the direction of the injector axis 27 is disposed next to the injector body 2 and delimits the interior space in the direction of the injector axis 27. The cap 11 can have only a single cap opening which is disposed facing away from the end wall 32.

As can be seen from FIGS. 1 to 12, the second piston 9 can have a piston opening 26 on its end face facing the opening 7, through which the first piston 8 extends into the interior of the second piston 9 and on which the first piston 8 is mounted in the decoupling state so as to be longitudinally displaceable relative to the second piston 9.

Figure 2:
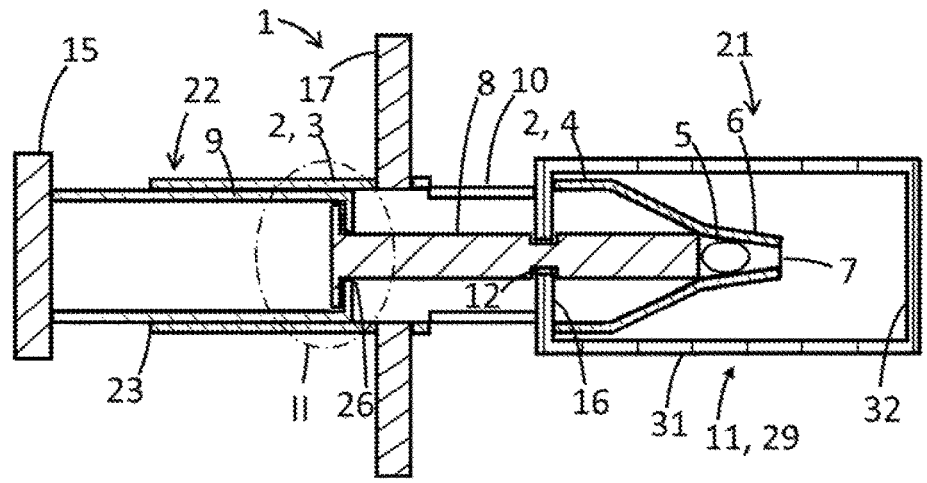
FIG. 2 shows the longitudinal sectional illustration from FIG. 1 at a second point in time.
Figure 3:
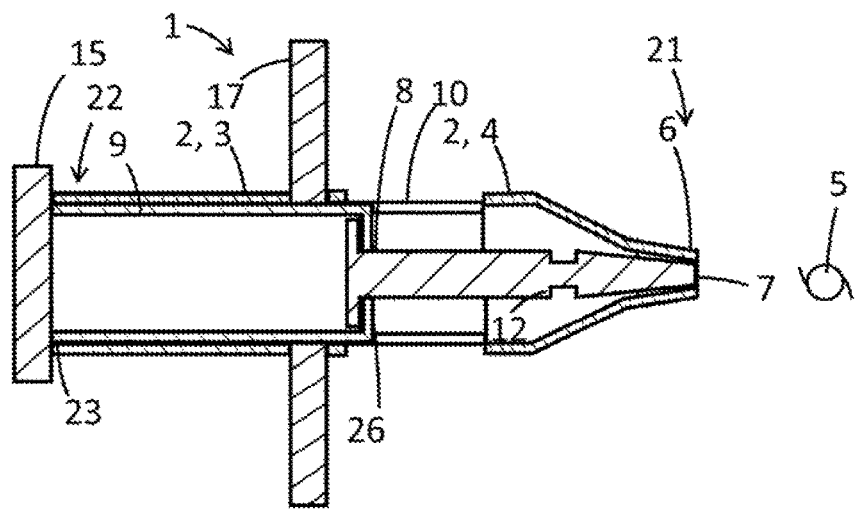
FIG. 3 shows the longitudinal sectional illustration from FIG. 1 at a third point in time.
Figure 4:
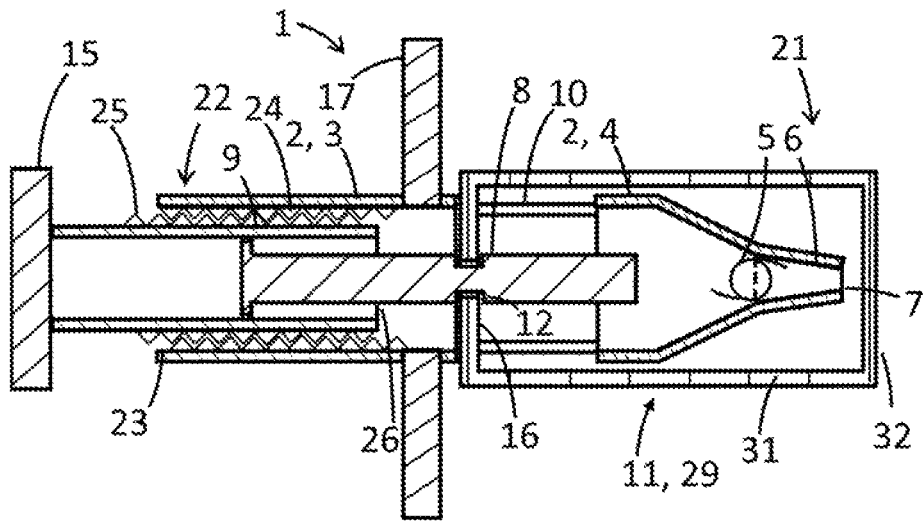
FIG. 4 shows a longitudinal sectional illustration in a view from above through a second embodiment of the injector according to the disclosure at a first point in time.
Figure 5:
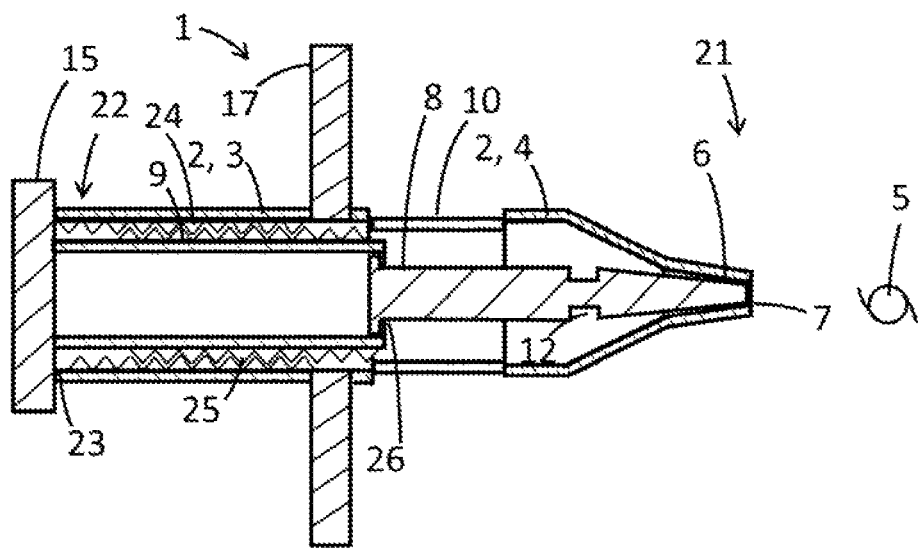
FIG. 5 shows the longitudinal sectional illustration from FIG. 4 at a second point in time.

In a first embodiment of the injector 1 according to the disclosure, which is shown in FIGS. 1 to 3, and in the second embodiment of the injector 1, which is shown in FIGS. 4 and 5, the injector body 2 has an injector body clearance 10, wherein the handle 29 extends through the injector body clearance 10 into the interior of the injector body 2 and is directly coupled to the first piston 8. In the event that the handle 29 has the cap 11 with the casing 31, the cap 11 can have a cap protrusion 16 (see FIGS. 1, 2 and 4) which is a part of the handle 29, projects radially inward from the casing 31 and engages with the first piston 8. The handle 29 can be releasably coupled to the first piston 8. For this purpose, the first piston 8 can have a piston groove 12 in which the handle 29 engages.

In FIGS. 1 and 4, the injector 1 is illustrated in the decoupling state of the first piston 8 and of the second piston 9 at the first point in time of the first embodiment and at the first point in time of the second embodiment. In that the handle 29 is now displaced away from the proximal end 23, for example by gripping the injector handle 17 with one hand and gripping the handle 29 with another hand and both hands being moved away from one another, the first piston 8 and the second piston 9 can be brought into the coupling state, which is illustrated at the second point in time of the first embodiment according to FIG. 2. In this case, the intraocular lens 5 can also be displaced in the direction of the opening 7. FIGS. 1 to 5 show that the injector body clearance 10 can have a distal end which is formed by the injector body 2 and on which the handle 29 can impact (cf. FIG. 2) when the handle 29 is displaced away from the proximal end 23. If the handle 29 is thereafter moved farther away from the proximal end 23, that portion of the handle 29 that is disposed in the piston groove 12 can bend in the direction of the proximal end 23 and thus disengage from the piston groove 12. As a result, the handle 29 is no longer coupled to the first piston 8 and can therefore be removed from the injector body 2. This is illustrated at the third point in time of the first embodiment (see FIG. 3) and at the second point in time of the second embodiment (see FIG. 5).

At the third point in time of the first embodiment, cf. FIG. 3, and the second point in time of the second embodiment, cf. FIG. 5, in the coupling state the second piston 9 was displaced in the direction of the opening 7, as a result of which the first piston 8 was also displaced in the direction of the opening 7. In the process, the first piston 8 has displaced the intraocular lens 5 out of the injector through the opening 7. As is illustrated by way of example for the first embodiment, the second piston 9 can be specified to be longitudinally displaced by a pushing movement, in particular manually and without a motor, in the direction toward the opening 7. Alternatively, as is illustrated by way of example for the second embodiment, the second piston 9 can be specified to be longitudinally displaced by a screw movement, in particular manually and without a motor, in the direction toward the opening 7. For this purpose, the injector body 2 can have an internal thread 24 and the second piston 9 can have an external thread 25, wherein the internal thread 24 engages with the external thread 25.

Figure 6:
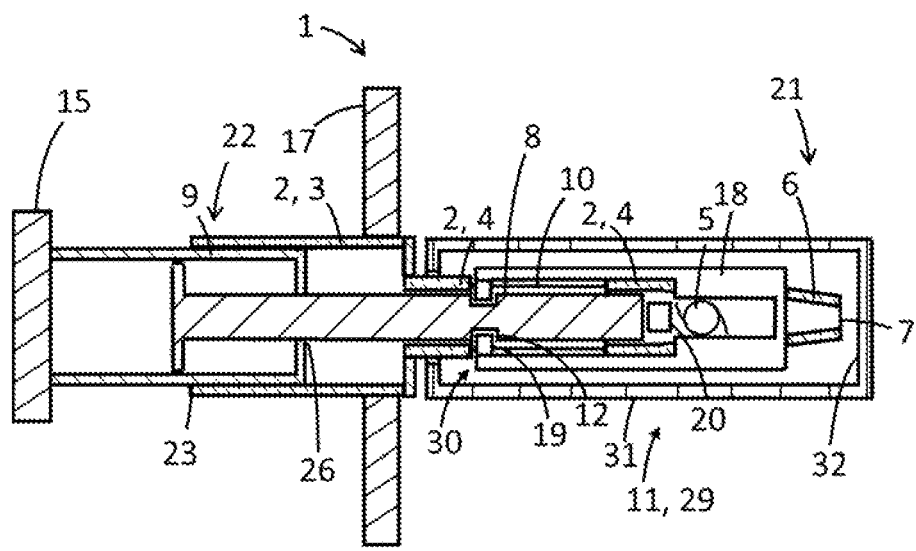
FIG. 6 shows a longitudinal sectional illustration in the view from above of a third embodiment of the injector according to the disclosure at a first point in time, wherein non-hatched components of the injector are not shown in a sectional view.
Figure 7:
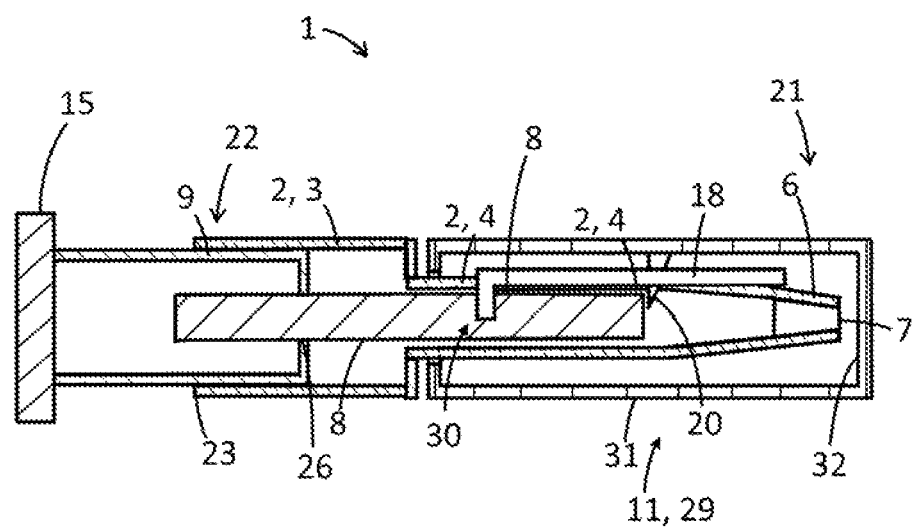
FIG. 7 shows a longitudinal sectional illustration in the lateral view of the third embodiment at the first point in time, as shown in FIG. 6, wherein non-hatched components of the injector are not shown in a sectional view.
Figure 8:
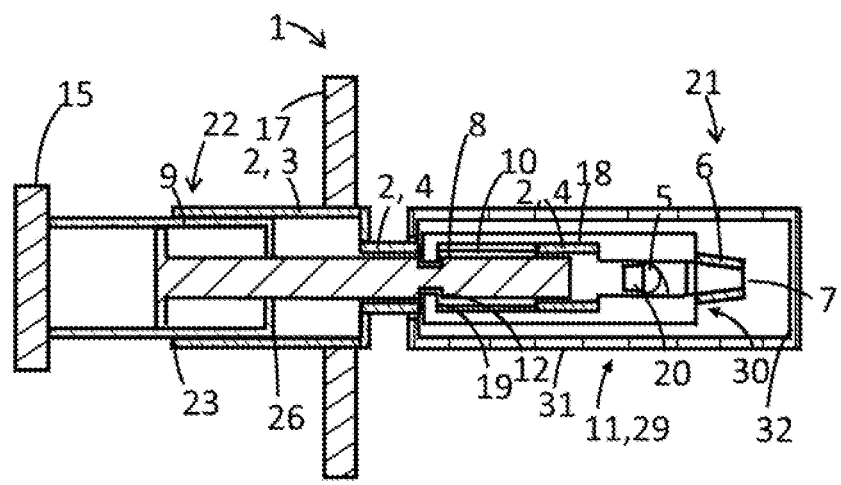
FIG. 8 shows the longitudinal sectional illustration from FIG. 6 at a second point in time.
Figure 9:
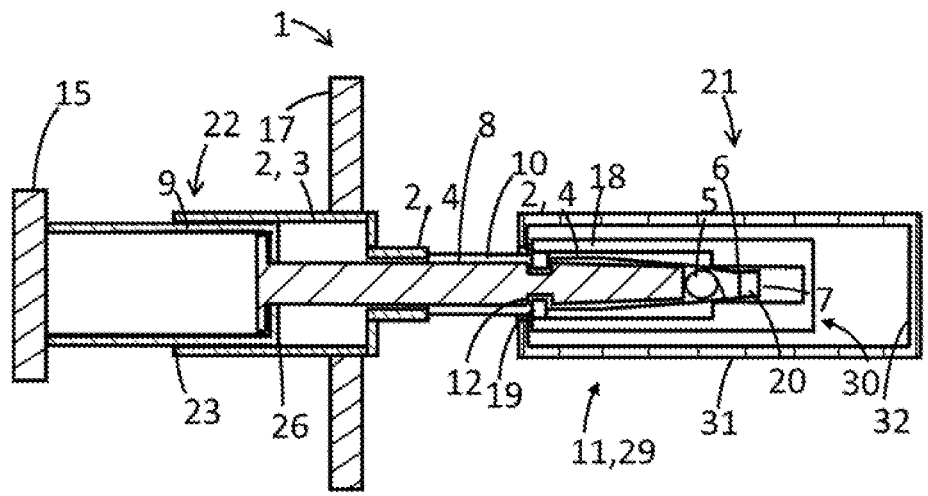
FIG. 9 shows the longitudinal sectional illustration from FIG. 6 at a third point in time.

FIGS. 6 to 10 show that the injector 1 according to the third embodiment can have a slide 30 which is disposed so as to be longitudinally displaceable on the injector body 2 and is directly coupled to the first piston 8, wherein when the handle 29 is displaced in the direction away from the proximal end 23, the handle 29 is specified to entrain the slide 30 so that the handle 29 is indirectly coupled to the first piston 8 by way of the slide 30. The slide 30 can have a lens holder 18 which is specified to hold the intraocular lens 5, wherein when the handle 29 is displaced away from the proximal end 23 and before the handle 29 entrains the slide 30, the handle 29 is specified to displace the intraocular lens 5 out of the lens holder 18 and fold the intraocular lens 5. For this purpose, the handle 29 can have a folding element 20, which projects from the remaining handle 29, protrudes into the injector body 2 and is specified to displace the intraocular lens 5 out of the lens holder 18 and fold the intraocular lens 5. The slide 30 and the folding element 20 are shown in the view from above in FIGS. 6 to 10, while all other components of the injector 1 are shown in the longitudinal sectional view. In FIGS. 6 and 7, the injector 1 is shown at a first point in time, at which the intraocular lens 5 is disposed in the lens holder 18 and the first piston 8 and the second piston 9 are in the decoupling state. In that the handle 29 is now displaced away from the proximal end 23, for example by gripping the injector handle 17 with one hand and gripping the handle 29 with another hand and both hands being moved away from one another, the handle 29 is displaced until the handle 29 impacts the slide 30 at a second point in time, as illustrated in FIG. 8. As can be seen from FIG. 8, the intraocular lens 5 was moved out of the lens holder 18 and is located below the folding element 20.

If the handle 29 is now displaced farther away from the proximal end 23, the handle 29 entrains the slide 30, due to the handle 29 having impacted the slide 30. In the process, the first piston 8 is also displaced in the direction of the opening 7, whereby the piston 8 contacts the intraocular lens 5 and displaces the latter in the direction of the opening 7. FIGS. 6 to 10 show that the injector body clearance 10 can have a distal end which is formed by the injector body 2 and on which the slide 30 can impact (cf. FIG. 9, which shows the injector 1 at a third point in time), when the handle 29 is displaced away from the proximal end 23.

FIGS. 5 to 9 show that the slide 30 can be releasably coupled to the first piston 8. For this purpose, the first piston 8 can have a piston groove 12 in which the slide 30 engages. In particular, the slide 30 can have a slide pin 19 which engages in the piston groove 12. If the handle 29 is moved farther away from the proximal end 23 after the third point in time, that portion of the slide 30 that is disposed on and in the piston groove 12 can be deformed in the direction of the proximal end 23 and thus disengage from the piston groove 12. As a result, the slide 30 is no longer coupled to the first piston 8 and can therefore be removed together with the handle 29 from the injector body 2. This is illustrated at the fourth point in time (see FIG. 10).

Figure 10:
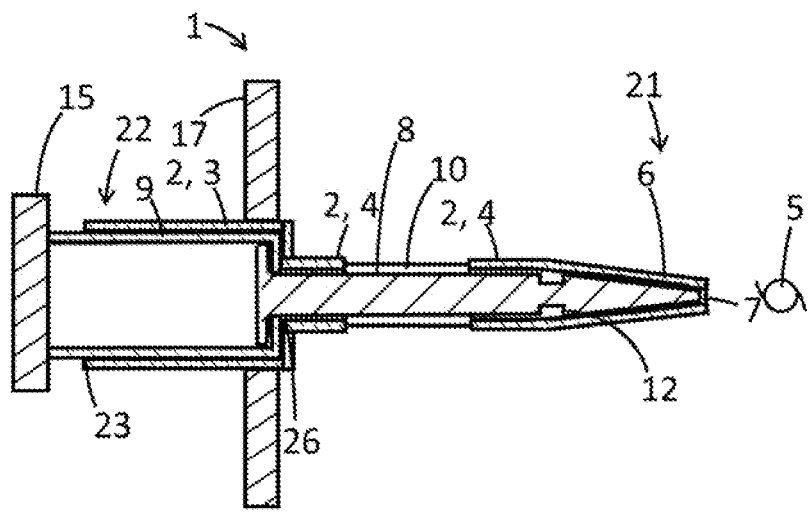
FIG. 10 shows the longitudinal sectional illustration from FIG. 6 at a fourth point in time.

At the fourth point in time, cf. FIG. 10, in the coupling state the second piston 9 was displaced in the direction of the opening 7, as a result of which the first piston 8 was also displaced in the direction of the opening 7. In the process, the first piston 8 has displaced the intraocular lens 5 out of the injector through the opening 7. The second piston 9 can be specified to be displaced longitudinally by a pushing movement, as is also shown for the third embodiment, or a screw movement in the direction of the opening 7.

Figure 11:
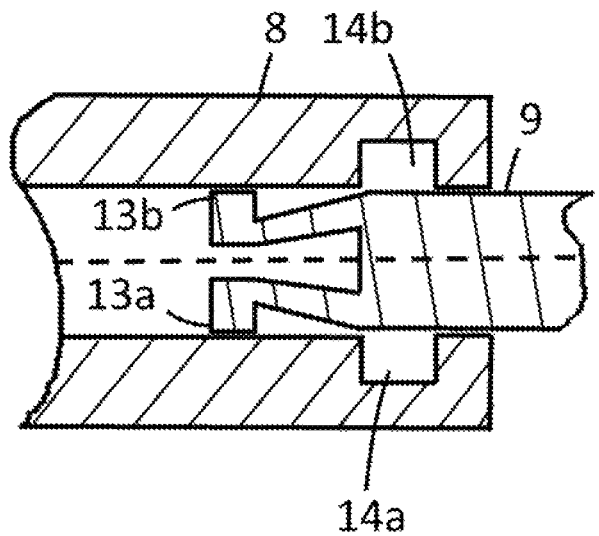
FIG. 11 shows an illustration of a detail I from FIG. 1, wherein a first piston and a second piston of the injector are in a decoupling state; and, FIG. 12 shows an illustration of a detail II from FIG. 2, wherein the first piston and the second piston are in a coupling state.
Figure 12:
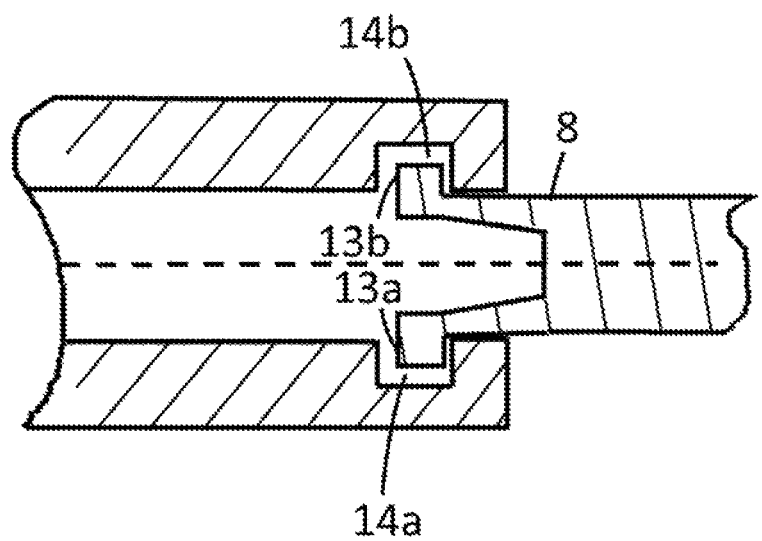

FIGS. 11 and 12 show that the first piston 8 can have a piston protrusion 13a and the second piston 9 can have a piston clearance 14a, wherein the piston protrusion 13a is specified to be disposed outside the piston clearance 14a when the first piston 8 and the second piston 9 are in the decoupling state (see FIG. 11), and specified to engage in the piston clearance 14a for bringing the first piston 8 and the second piston 9 into the coupling state (see FIG. 12) when the first piston 8 is displaced toward the opening 7. The piston clearance 14a can be incorporated in that side of the second piston 9 which is inside in the radial direction 33. The piston protrusion 13a can abut that side of the second piston 9 that is inside in the radial direction 33, when the piston protrusion 13a is disposed outside the piston clearance 14a, and as a result be pushed inward in the radial direction 33 and thus be under tension. When the first piston 8 is displaced toward the opening 7, the piston protrusion 13a enters the piston clearance 14a, whereby the piston protrusion 13a as a result is at least under less tension. FIGS. 11 and 12 moreover show that the first piston 8 can have a further piston protrusion 13b and the second piston 9 can have a further piston clearance 14b, wherein the further piston protrusion 13b is specified to be disposed outside the further piston clearance 14b when the first piston 8 and the second piston 9 are in the decoupling state (see FIG. 11), and specified to engage in the further piston clearance 14b for bringing the first piston 8 and the second piston 9 into the coupling state (see FIG. 12) when the first piston 8 is displaced toward the opening 7.

FIGS. 1 to 10 show that the injector 1 can include the intraocular lens 5. The intraocular lens 5 at the respective first point in time can be disposed in the injector body 2 and/or in the lens holder 18.

As can be seen from FIGS. 1 to 10, the second piston 9 on the distal end thereof can have a piston head 15. The piston head 15 can be specified to impact on the injector body 2 to delimit the movement of the second piston toward the opening 7.

FIGS. 6 to 10 show that the injector body 2 can have a cylinder 3 in which the second piston 9 is mounted so as to be longitudinally displaceable, and a cartridge 4 in which is disposed the first piston 9 for the longitudinal displacement of the intraocular lens 5. The cylinder 3 and the cartridge 4 can be releasably coupled to one another.

It is understood that the foregoing description is that of the preferred embodiments of the invention and that various changes and modifications may be made thereto without departing from the spirit and scope of the invention as defined in the appended claims.

LIST OF REFERENCE SIGNS

1 Injector
2 Injector body
3 Cylinder
4 Cartridge
5 Intraocular lens
6 Injector tip
7 Opening
8 First piston
9 Second piston
10 Injector body clearance
11 Cap
12 Piston groove
13a Piston protrusion
13b Further piston protrusion
14a Piston clearance
14b Further piston clearance
15 Piston head
16 Cap protrusion
17 Injector handle
18 Lens holder
19 Slide pin
20 Folding element
21 Distal region
22 Proximal region
23 Proximal end
24 Internal thread
25 External thread
26 Piston opening
27 Injector axis
28 Circumferential direction
29 Handle
30 Slide
31 Casing
32 End wall
33 Radial direction

The invention claimed is:

1. An injector for inserting an intraocular lens into a capsular bag of an eye, the injector defining an injector axis and comprising:
    an injector body having an injector tip defining an opening;
    said injector body further having a proximal end defining a proximal end region with said proximal end facing away from said opening and having a distal end defining a distal end region;
    a first piston directed toward said opening and being configured to contact and displace said intraocular lens;
    a second piston disposed in said proximal end region and being configured to be operable from outside of said injector;
    said first piston and said second piston each being configured to be longitudinally displaceable along said injector axis in said injector body so as to be movable between a decoupling state and a coupling state;
    said first and second pistons are in said decoupling state when said first and second pistons are displaceable longitudinally relative to each other and conjointly define a first longitudinal extent along said injector axis; and, said first and second pistons are in said coupling state when said first and second pistons are rigidly coupled together in a direction of said injector axis and said first and second pistons conjointly define a second longitudinal extent along said injector axis greater than said first longitudinal extent; and, a handle disposed in said distal end region of said injector body and being movable relative to said injector body and being configured to be manually operated from outside of said injector and to be coupled to said first piston so that when said pistons are in the decoupling state, said first piston is displaced toward said opening and relative to said second piston by manually moving said handle relative to said injector body along said injector axis away from said proximal end such that said first and second pistons are brought into said coupling state and, by way of contact between said first piston and said intraocular lens, causing said intraocular lens to be shifted in said injector tip toward said opening.

2. The injector of claim 1, wherein said injector body has an injector body clearance; and, said handle is configured to extend through said injector body clearance into an interior of the injector body and is directly coupled to said first piston.

3. The injector of claim 2, wherein said handle is releasably coupled to said first piston.

4. The injector of claim 1, wherein said injector has a slide longitudinally displaceable on said injector body and is directly coupled to said first piston; and, when said handle is displaced away from said proximal end of said injector body, said handle is configured to entrain said slide causing said handle to be indirectly coupled to said first piston by way of said slide.

5. The injector of claim 4, wherein said slide has a lens holder configured to hold said intraocular lens; and, when said handle is displaced away from said proximal end of said injector body and before said handle entrains said slide, said handle is configured to displace said intraocular lens out of said lens holder and fold said intraocular lens.

6. The injector of claim 4, wherein said slide is releasably coupled to said first piston.

7. The injector of claim 1, wherein said handle has a cap delimiting an interior space wherein said injector body is disposed.

8. The injector of claim 7, wherein said cap extends in a direction of said injector axis from said injector body beyond said opening.

9. The injector of claim 8, wherein said cap has a casing delimiting said interior space in a radial direction with respect to said injector axis; and, said injector further comprises an end wall which, in the direction of the injector axis, is disposed next to said injector body and delimits said interior space in the direction of said injector axis.

10. The injector of claim 1, wherein said second piston on an end side thereof facing said opening has a piston opening by way of which said first piston extends into the interior of said second piston and whereon said first piston in said decoupling state is mounted so as to be longitudinally displaceable relative to said second piston.

* * * * *